United States Patent [19]

Williams

[11] Patent Number: 5,496,740
[45] Date of Patent: Mar. 5, 1996

[54] METHOD AND APPARATUS FOR DETERMINING THE CONCENTRATION OF COMPONENTS OF LIQUID SYSTEMS

[75] Inventor: Paul M. Williams, Barry, United Kingdom

[73] Assignee: Lion Laboratories PLC, Barry, United Kingdom

[21] Appl. No.: 199,322

[22] PCT Filed: May 14, 1992

[86] PCT No.: PCT/GB92/00864

§ 371 Date: Mar. 2, 1994

§ 102(e) Date: Mar. 2, 1994

[87] PCT Pub. No.: WO93/05893

PCT Pub. Date: Mar. 18, 1993

[30] Foreign Application Priority Data

Sep. 4, 1991 [GB] United Kingdom ............... 9118913

[51] Int. Cl.[6] .................................. G01N 33/48
[52] U.S. Cl. .............. 436/132; 436/900; 422/84; 422/98; 128/719
[58] Field of Search .................. 422/84, 85, 80, 422/82.01, 98; 436/132, 900; 128/719, 730

[56] References Cited

U.S. PATENT DOCUMENTS

| 3,509,771 | 5/1970 | Moberg et al. | |
|---|---|---|---|
| 3,609,838 | 9/1972 | Luckey. | |
| 4,617,821 | 10/1986 | Yokoyama et al. | 422/84 X |
| 4,749,553 | 6/1988 | Lopez et al. | 422/84 |
| 4,900,514 | 2/1990 | Fuller | 422/84 |
| 4,996,161 | 2/1991 | Conners et al. | 422/84 X |
| 4,997,770 | 3/1991 | Giles et al. | 436/900 X |

FOREIGN PATENT DOCUMENTS

| 10970/88 | 8/1988 | Australia. |
| WO87/07724 | 12/1987 | WIPO. |
| WO90/02331 | 3/1990 | WIPO. |

Primary Examiner—Jeffrey R. Snay
Attorney, Agent, or Firm—Young & Thompson

[57] ABSTRACT

Testing apparatus is provided in the form of a pen and has a body 11 and cap 12. The body 11 has an inlet 13 at its tip which communicates with a fuel cell chamber 14, containing a fuel cell 15, and, via that chamber, with a passage 16 and a cylinder 17. A piston 18 is mounted in the cylinder 17 for operation by a button 19, a spring 21 and latch 22 such that it can draw air through the inlet 13 to the fuel cell 15. If the inlet 13 is placed in a user's mouth the apparatus can provide an indication of his breath alcohol concentration, for example, on display 23.

14 Claims, 2 Drawing Sheets

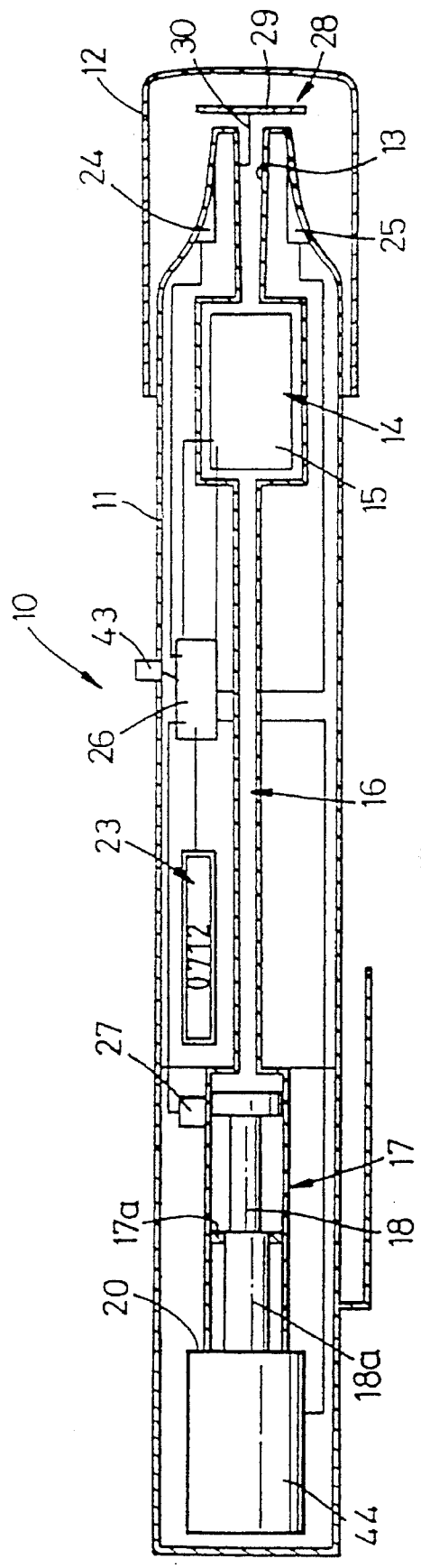

METHOD AND APPARATUS FOR DETERMINING THE CONCENTRATION OF COMPONENTS OF LIQUID SYSTEMS

This invention relates to methods and apparatus for determining the concentration of volatile oxidisable components of liquid systems and in particular, but not exclusively, for the detection of body alcohol concentration.

Throughout much of the World the penalties for driving whilst under the influence of alcohol are steadily increasing and this has lead to a need for apparatus which will enable individuals to determine their body alcohol concentration with accuracy. A wide range of "self testers" have accordingly come on to the market, but in general those which are relatively cheap are dangerously inaccurate and it is difficult to find any viable apparatus; below £100.

In addition there are other circumstances where alcohol content is of interest to ordinary members of the public, for example in home brewing and home wine making.

From one aspect of the invention there is provided apparatus for measuring volatile oxidisable or reducible components of a liquid system, comprising a body having an inlet insertable in a head space over the liquid system, an electrical sensor, means for drawing a sample from the head space through the inlet into the sensor and means for displaying the component concentration in the liquid system detected by the sensor.

It will be appreciated that the body can contain all of the elements of this apparatus and conveniently the body may be made generally in the form of a pen or syringe so that it can be readily carried in the user's pocket. In that case the inlet is preferably formed at or adjacent one end.

Such a construction is particularly convenient if the apparatus is to be used for self-testing for body alcohol concentration because it enables an entirely novel procedure for testing. This is based on the fact that alcohol disperses equally throughout all the body fluids including saliva. The Applicant has realised that when closed a person's mouth is the equivalent of a head space vessel and that a known concentration of the alcohol in the saliva will evaporate into the air contained within a closed mouth until equilibrium is achieved. Tests have shown that this is in around 20 seconds dependent on the ambient and mouth temperature. Measurements may be made either above or below the tongue.

Thus if the user places the inlet into his mouth and closes his lips around the body he can draw off a sample of the air, after a 20 second wait, into the sensor and thus achieve a reading of his body alcohol concentration.

In the light of this, the sample drawing means may comprise a spring-loaded or motor driven/piston or diaphragm disposed within a cylinder in the body which is in communication with the inlet and the sensor. Detent means may be provided for retaining the piston or diaphragm in a set or pre-sampling position and the detent may either be manually releasable or it may be automatically released. In the latter case the detent release may occur in response to some detection of the ambient conditions in the mouth. Thus it is preferred that the apparatus also includes a thermistor, or other temperature detecting device, which will detect when the air in the user's mouth reaches a predetermined temperature, for example normal body temperature. This will not only be an indication that the mouth has been closed for a sufficient period but will also overcome problems that arise due to the temperature dependence of the alcohol content of the air. Additionally or alternatively the body may be provided with a photoelectric cell, or other light detection device, which will detect when the mouth is fully closed.

Additionally or alternatively it may set a timer. In order to keep the apparatus as cheap as possible it may be desirable to cause the thermistor and/or for the photo-electric cell to light an indicating light or activate an audible warning such as a buzzer or beeper on the body rather than cause automatic releasing of the piston or the like. In this case the user will manually release the detent or operate the switch when the light is illuminated or the beeper sounds. Conveniently the piston can be manually reset, much in the manner of a retractable pen. Similarly the release mechanism and detent can be the equivalent of the old style click release ballpoint pen.

It is conceivable that the piston can be released by the normal reset button as on modern retractable pens, but then the speed of its withdrawal will be dependent on the user and the sampling may not be as effective. In another approach the piston may be driven by a micro-electric motor or replaced by a spring-loaded diaphragm. In the former case the button may operate an electric switch.

Sampling errors could occur if the piston caused saliva to be drawn in through the inlet or if saliva was splashed into the inlet. To avoid this a shield may be provided overlying the inlet and leaving an annular or part-annular space through which air may be drawn in. Additionally or alternatively the return of the piston may be controlled so that the suction created at the inlet is relatively low and insufficient to draw in a liquid.

The apparatus as described may also be used to take a sample of exhaled breath either in the mouth or adjacent the lips. In this case a timer may be provided so that the sample is taken from deep lung breath.

In an alternative construction the inlet may be provided with a cannula or the like. This would be particularly useful for sampling head space air in demi-johns and other home brewing equipment as the cannula could be introduced through a bung or seal without exposing the vessel to a significant ingress of air. Alternatively a sample of the beer or wine could be placed in a suitable head space vessel.

In this case particularly it may be simpler to replace the piston mechanism described above with a simple syringe mechanism as the head space should already be at equilibrium.

The invention also consists in a method of obtaining an indication of body alcohol concentration, comprising inserting a sampling inlet into the user's mouth, closing the mouth around the inlet for a sufficient period to reach equilibrium in the air trapped in the mouth, sampling the trapped air and feeding the sample to an electrical gas sensor for providing an indication of the alcohol content of the breath and hence of the user's body.

The period may be between 15 and 30 seconds but is preferably between around 18 and 25 seconds. It is thought that the period should not be overlong because nasal breathing may effect the reading. In addition it is preferred that the user swallows before starting the test so that the air trapped in the mouth is initially fresh. Swallowing also removes excess saliva from the mouth.

Although the invention has been defined above it is to be understood that it includes any inventive combination of the features set out above or in the following description.

The invention may be performed in various ways and specific embodiments will now be described, by way of example, with reference to the accompanying drawings, in which:

FIG. 4 is a part-sectional view of a still further alternative construction of the apparatus of FIG. 1.

Figure 1:
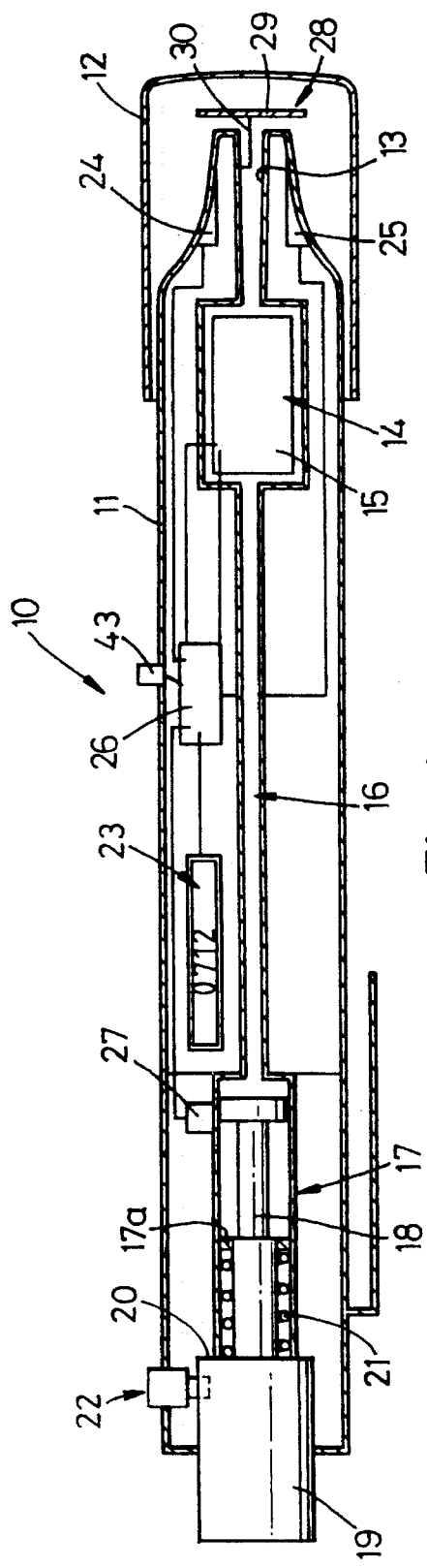
FIG. 1 is a part-sectional view of testing apparatus.

The testing apparatus 10 shown in FIG. 1, and which is generally in the form of a pen, comprises a body 11 and a cap 12. The body has an inlet 13 at its tip which communicates with a fuel cell chamber 14, containing a fuel cell 15, and, via that chamber, with a passage 16 and a cylinder 17. A piston 18 is slidably mounted in the cylinder 17 and has a button shaped projection 19 which extends through the end of the body 11. The button 19 defines an abutment 20 and the cylinder has a wall 17a between which a spring 21 can act in a sense to urge the piston 18 in a leftward direction along the cylinder 17, i.e. in a sense to draw air through the inlet 13, chamber 14 and passage 16. The piston 18 can be held in its set position, as shown in FIG. 1, by a releasable latch generally indicated at 22.

The fuel cell 15 is electrically connected to a display 23 for indicating the alcohol level detected by the fuel cell. At its tip the body 11 is also provided with a thermistor 24 and/or a photo-electric cell 25 for detecting the conditions in the mouth as previously described.

The body also contains a microprocessor 26 for controlling the apparatus. This microprocessor 26 is responsive not only to the fuel cell 15 but also to the thermistor cell 24, the photo-electric cell 25 and to a position detector 27, which detects whether or not the piston 18 is in its set position.

Thus in use the user presses the set button 19 to trigger the piston 18 which is held in its set position by the latch 22 and is detected by the detector 27. The microprocessor 26 causes the word WAIT to appear on the display 23 whilst taking a reading from the fuel cell 15 to carry out a calculation to see if there is any residual alcohol within the fuel cell. If there is a zero reading then the user will be told to proceed with the test, but if there is a non-zero reading the user will wait until the microprocessor indicates that a test may proceed.

Once the TEST instruction appears on the display 23, the user places the device in his mouth and carries out the procedure described above to obtain a sample of the air in his mouth once certain conditions are met. The fuel cell then calculates the alcohol content of that breath sample and displays the result on the display 23.

The microprocessor can be enabled to initiate the TEST procedure by either the thermistor 24 and/or photo-electric cell 25 and preferably both. Where the ambient temperature is below mouth temperature the thermistor 24 will indicate a characteristic rate of rise in temeperature to a constant and this alone can be used. Alternatively, the microprocessor may begin the TEST procedure after a predetermined time from the photo-electric cell 25 detecting mouth closure. Preferably, however, both conditions are required so as to prevent false readings due to particularly high or particularly low ambient temperatures.

As mentioned above a saliva or drip shield is required and one such construction is illustrated at 28. This comprises a disc 29 supported above the inlet 13 on a stalk 30.

Figure 2:
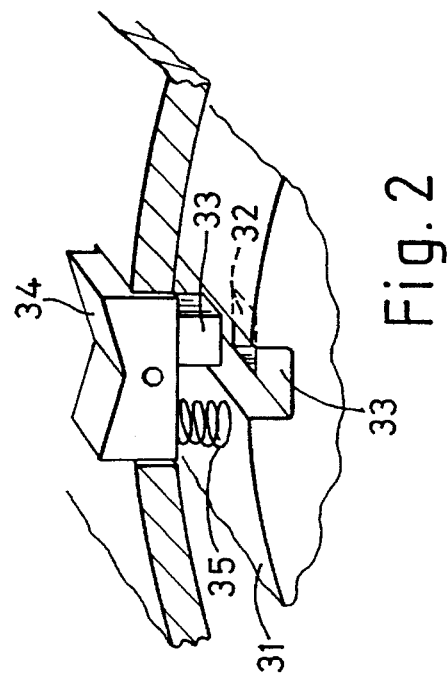
FIG. 2 is a detail of a release button of the apparatus of FIG. 1.

Turning to FIG. 2 a possible construction of the release mechanism 22 is illustrated. Here it will be seen that the button 19 is apertured at 32 so that in the depressed position a detent 33 on the release button 34 engages in the aperture 32 to hold the piston depressed. The button 34 is in the form of a spring-loaded rocker switch and the piston 18 can be released by depressing the switch against the action of the spring 35.

As well as being suitable for self testing the apparatus 10 has the additional advantage that it can be used, very simply, to take a measurement from an unconscious person.

In an alternative arrangement the spring and latch mechanism may be replaced by a battery driven micro-electric motor in which case the button 19 may operate an electric switch. However, as shown in FIG. 4, the motor 44 could be entirely controlled by the microprocessor 26 which would be enabled by the thermistor and/or photo-electric cell as described above. Normally an on/off switch would be provided. The motor 44 would be fixed on the cylinder 17 and drive rectilinearly the piston 18 through its rod extension 18a. In a still further construction the piston may be replaced by a spring-loaded diaphragm.

Figure 3:
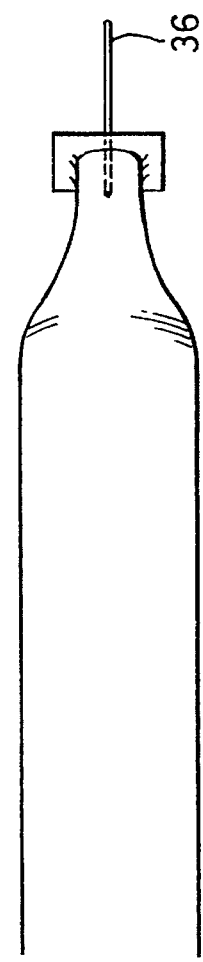
FIG. 3 is a schematic representation of an alternative construction of the apparatus of FIG. 1.

FIG. 3 illustrates a construction where the tip of the body 11 is modified for use in home brewing or other circumstances where alcohol is contained within a vessel. In particular it will be seen that the inlet 13 is provided with a cannula 36. The use of the apparatus is otherwise more or less identical, although, as mentioned above, in many instances equilibrium will already have been reached in the vessel. As the vessel will not be kept at a more or less constant temperature as is the case with the human body temperature, compensation means, such as the thermistor may be built in to the device.

I claim:

1. Apparatus for measuring the concentration of a volatile component in a person's breath, which is in equilibrium with their saliva, comprising a body having an inlet of a size adapted to be inserted into a user's mouth such that the person's mouth can close around the body to form a mouth head space, an electric sensor for measuring the volatile component, means for drawing a sample, through the inlet, from the mouth head space to the sensor, means for determining when a predetermined period of time has elapsed after the user's mouth is closed around the inlet, means for displaying the volatile component concentration of the breath in the mouth head space measured by the sensor, wherein the apparatus is self-contained within the body.

2. Apparatus as claimed in claim 1, wherein said determining means comprises a light detection device for determining when the person's mouth is closed around the inlet, and wherein the sample drawing means only operate when a predetermined time has elapsed after the user's mouth has closed around the inlet.

3. Apparatus as claimed in claim 1, further including a shield overlying the inlet and defining an annular or part-annular opening.

4. Apparatus as claimed in claim 1, wherein the sample drawing means is arranged such that the suction created at the inlet is insufficient to draw in a liquid.

5. Apparatus as claimed in claim 1, wherein the inlet is at or adjacent one end of the body.

6. Apparatus as claimed in claim 5, wherein the body is generally pen-shaped.

7. Apparatus as claimed in claim 5, wherein the body is in the form of a syringe.

8. Apparatus as claimed in claim 1, wherein said determining means comprises means for detecting when air in the person's mouth reaches a predetermined or constant temperature and means for operating the sample drawing means when this temperature is detected.

9. Apparatus as claimed in claim 8, wherein said determining means comprises a light detection device for determining when the person's mouth is closed around the inlet and wherein the sample drawing means only operate when the user's mouth is closed.

10. Apparatus as claimed in claim 9, wherein the sample drawing means only operates when the user's mouth is closed and the predetermined or constant temperature is detected.

11. A method of obtaining an indication of body alcohol concentration of a person's breath, comprising inserting a sampling inlet into the person's mouth, closing the mouth around the inlet for a sufficient period for the air trapped in the mouth to equilibrate with the person's saliva, drawing a sample of the trapped air through said inlet and feeding the sample to an electrical gas sensor for providing an indication of the alcohol content of the person's breath and hence of the person's body.

12. A method as claimed in claim 11, wherein the period is between 15 and 30 seconds.

13. A method as claimed in claim 11, wherein the period is between 18 and 25 seconds.

14. A method as claimed in claim 11, wherein the user swallows prior to the insertion of the inlet into their mouth.

* * * * *